United States Patent [19]
Hershberger et al.

[11] Patent Number: 5,423,822
[45] Date of Patent: Jun. 13, 1995

[54] METHOD AND APPARATUS FOR PREPARING A BONE FOR RECEIVING A PROSTHETIC DEVICE

[75] Inventors: Troy W. Hershberger, Warsaw; David R. Brown, Leesburg, both of Ind.

[73] Assignee: Biomet, Inc., Warsaw, Ind.

[21] Appl. No.: 9,815

[22] Filed: Jan. 27, 1993

[51] Int. Cl.⁶ .................... A61B 17/00; A61F 2/32
[52] U.S. Cl. ............................. 606/79; 606/80
[58] Field of Search ............... 606/79, 80, 88; 408/115 B, 241 B, 72 B; 51/205 WG, 210

[56] References Cited

U.S. PATENT DOCUMENTS

| | | | |
|---|---|---|---|
| 2,423,164 | 7/1947 | Williams | 408/115 B |
| 4,211,228 | 7/1980 | Cloutier | |
| 4,306,550 | 12/1981 | Forte | |
| 4,421,112 | 12/1983 | Mains et al. | |
| 4,467,801 | 8/1984 | Whiteside | 606/80 X |
| 4,474,177 | 10/1984 | Whiteside | 606/80 |
| 4,487,203 | 12/1984 | Androphy | |
| 4,502,483 | 3/1985 | Lacey | |
| 4,722,330 | 2/1988 | Russell et al. | |
| 4,907,578 | 3/1990 | Petersen | 606/79 |
| 5,002,545 | 3/1991 | Whiteside et al. | 606/80 |
| 5,053,037 | 10/1991 | Lackey | |
| 5,169,401 | 12/1992 | Lester et al. | 606/80 X |

FOREIGN PATENT DOCUMENTS 2063730  10/1981  United Kingdom ............ 408/241 B

OTHER PUBLICATIONS

Buechel, Frederick F., "New Jersey Tricompartmental Total Knee System Surgical Procedure" DePuy brochure (undated).
"The Howmedica Universal Total Knee Instrument System" Howmedica brochure, 1980.
"The Howmedica Universal Total Knee Instrument System", Howmedica brochure (undated).
Lunceford, Emmett M., "The Modified Austin Moore Design with Porocoat", DePuy brochure, 1981.
Whiteside, Leo A., "Whiteside Ortholoc Total Knee System", Dow-Corning-Wright brochure, 1983.
"T.A.R.A. Articular Replacement System for Hemi and Total Hip Arthroplasty", DePuy brochure (undated).
Portion of brochure identified as "Final Preparations", Dow-Corning-Wright brochure, pp. 28-33 (undated).
"A Common Sense Instrumentation Approach To Achieving Accurate Knee Replacement Alignment, Balance and Collateral Ligament Tensioning", Biomet brochure, Apr. 1982.
Portion of brochure identified as "Special Techniques for Dealing With Severe Deformity," Dow-Corning-Wright brochure, pp. 34-42 (undated).

*Primary Examiner*—Steven A. Bratlie
*Attorney, Agent, or Firm*—Harness, Dickey & Pierce

[57] ABSTRACT

A planer for shaping a bone prior to receiving a prosthetic device. The planer includes a surface which is able to abrade the bone. In addition, the planer is operable to engage one of a plurality of positioning members which are able to orient the surface of the planer at an angle which corresponds to the valgus angle of the bone.

19 Claims, 4 Drawing Sheets

METHOD AND APPARATUS FOR PREPARING A BONE FOR RECEIVING A PROSTHETIC DEVICE

BACKGROUND OF THE INVENTION

The present invention relates generally to the implantation of prosthetic devices, and more particularly to a method and apparatus for preparing a bone for receiving a prosthetic device.

The hyaline articular cartilage of a natural knee joint may undergo degenerative changes due to various etiologies. When these degenerative changes are advanced, it may ultimately become necessary to replace the natural knee joint with an artificial knee joint prosthesis. A knee joint prosthesis typically comprises a femoral component and a tibial component. The femoral component and tibial component are designed to be surgically attached to the distal end of the femur and proximal end of the tibia respectively. After being surgically attached, the femoral component is able to engage the tibial component in such a manner as to simulate the articulating motion of an anatomical knee joint.

When preparing the femur and tibia for receiving a knee joint prosthesis, it is important that the components of the knee joint prosthesis be properly positioned on the femur and tibia to minimize the possibility that complications may result. To facilitate proper positioning of the femoral component of the knee joint prosthesis, the orientation of the intramedullary canal of the femur is often used as a reference point when determining the manner in which the distal femoral surface should be shaped. In this regard, it is a common practice to prepare an anterior-posterior radiograph of the femur prior to surgery. The angle of the intramedullary canal of the femur relative to the vertical axis of the body (i.e., the valgus angle of the femur) is then determined. An intramedullary rod is then inserted into the intramedullary canal of the femur. The intramedullary rod generally includes an angled portion which is angularly displaced from the main portion of the rod by an angle equivalent to the valgus angle. The angled portion of the intramedullary rod is then used to orient various shaping instruments which are used when the distal femoral surface is resected. In this regard, several different cutting guides and a planer may be secured to the angled portion of the intramedullary rod to ensure that the shape of the resected femur reflects the valgus angle of the femur.

While the method described above is effective in shaping the distal end of the femur to receive the femoral component of a knee joint prosthesis, there are nevertheless several disadvantages associated with using this method. For example, because the intramedullary rod generally includes an angled portion, the intramedullary rod is often relatively difficult to insert into the intramedullary canal. This is because it is generally difficult to impact the angled portion of the intramedullary rod in a direction which is displaced from the axial centerline of the angled portion. A further disadvantage of the method described above is that a complete set of surgical instruments for implanting a knee joint prosthesis must generally include a number of different intramedullary rods having different angled portions, one for each possible range of valgus angles. This is complicated by the fact that shorter intramedullary rods may sometimes be necessary when an existing hip implant is present, thereby increasing the number of intramedullary rods which are necessary to form a complete set of instruments. While a planer which is operable to engage a straight alignment guide has been used for preparing a tibial surface to receive a prosthetic device as is shown in U.S. Pat. No. 4,467,801, such a planer does not provide means for orienting the abrading surface of the planer at a plurality of different angular positions which is required for preparing a femur for receiving a prosthetic device.

SUMMARY OF THE INVENTION

According to one embodiment of the present invention, a set of surgical instruments is provided for shaping a bone prior to receiving a prosthetic device. The set of surgical instruments comprises an intramedullary rod which is operable to be secured to the bone. In addition, the set of surgical instruments includes a planer which is operable to engage the intramedullary rod. The planer is able to selectively abrade the bone at one of a plurality of selectable angular orientations with respect to the intramedullary rod.

According to another embodiment of the present invention, a method is provided for shaping a bone prior to receiving a prosthetic device. The method comprises the steps of initially securing an intramedullary rod to the bone and then resecting the bone. A planer is then located adjacent to the bone at one of several selectable angular orientations with respect to the intramedullary rod. After the planer is rotated so as to abrade the bone, additional cuts are made to the bone so as to permit the bone to receive the prosthetic device.

An advantage of the present invention is to provide a method and apparatus for preparing a femur for receiving the femoral component of a knee joint prosthesis which uses a single intramedullary rod for orienting various shaping instrumentation at one of a number of possible valgus angles.

A further advantage of the present invention is to provide a method and apparatus for preparing a femur for receiving the femoral component of a knee joint prosthesis which is able to facilitate proper positioning and functioning of the knee joint prosthesis.

Another advantage of the present invention is to provide a method and apparatus for preparing a femur for receiving the femoral component of a knee joint prosthesis which uses an intramedullary rod of a shape which is able to be relatively easily inserted into the intramedullary canal of the femur.

Another advantage of the present invention is to provide a method and apparatus for preparing a bone for receiving a prosthetic device which is relatively easy to use and which is relatively low in cost.

BRIEF DESCRIPTION OF THE DRAWINGS

Various additional advantages of the present invention will become apparent to one skilled in the art by reading the following specification and subjoined claims and by referencing the following drawings in which:

DETAILED DESCRIPTION OF THE PREFERRED EMBODIMENT

The following discussion of the preferred embodiment of the present invention is merely exemplary in nature and is in no way intended to limit the invention or its application or uses.

Figure 1:
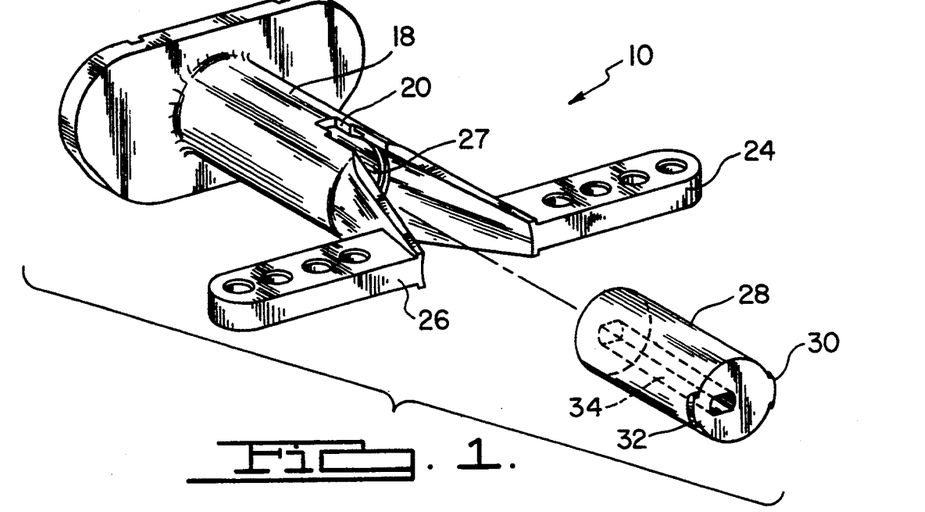
FIG. 1 is an exploded prospective view of the femoral planer according to the teachings of the preferred embodiment of the present invention.
Figure 2:
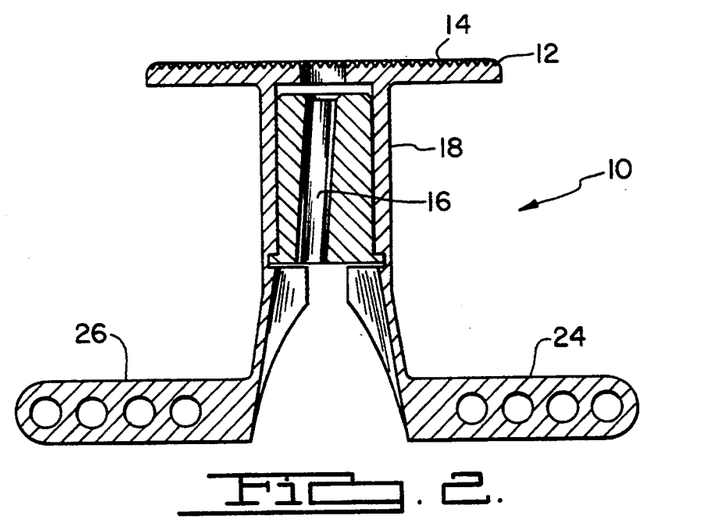
FIG. 2 is a cross-sectional view of the femoral planer shown in FIG. 1 according to the teachings of the preferred embodiment of the present invention.
Figure 3:
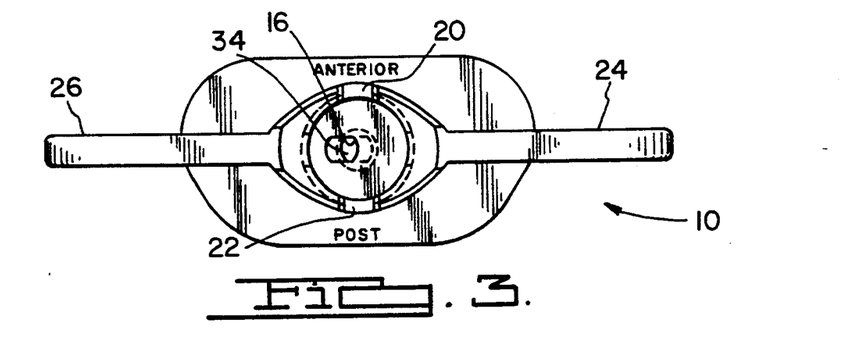
FIG. 3 is an end view of the femoral planer shown in FIG. 1 according to the teachings of the preferred embodiment of the present invention.

Referring to FIG. 1, a femoral planer 10 is shown according to the teachings of the preferred embodiment of the present invention. The femoral planer 10 is used to smooth the distal surface of the femur at an angle which corresponds to the valgus angle of the femur. The femoral planer 10 includes an abrading surface 12 which has a plurality of spaced cutting ridges 14 disposed thereon. The abrading surface 12 is operable to abrade the distal surface of the femur upon rotation of the femoral planer 10.

The femoral planer 10 further includes an aperture 16 which is used to allow insertion of an intramedullary rod, which is described below, into the femoral planer 10. In addition, the femoral planer 10 also includes a cylindrical portion 18 which is used to accept a positioning member which is also described below. Disposed on the cylindrical portion 18 are a plurality of notched portions 20 and 22. The notched portions 20 and 22 are used to receive the flanges of the positioning member when the positioning member is inserted into the cylindrical portion 18. Also disposed within the cylindrical portion 18 is an internal radial groove 27 which is located adjacent to the notched portions 20 and 22. As discussed below, the internal radial groove 27 permits the cylindrical portion 18 to rotate with respect to the positioning member. The femoral planer 10 further includes handles 24 and 26 which are used to rotate the femoral planer 10.

To provide means for orienting the abrading surface 12 of the femoral planer 10 at a plurality of selectable angular orientations, a positioning member 28 is provided. The positioning member 28 is used to orient the femoral planer 10 with respect to the intramedullary rod as a function of the valgus angle of the femur. To provide means for permitting limited movement of the positioning member 28 with respect to the abrading surface 12, the positioning member 28 includes a plurality of flanges 30 and 32 which are operable to be disposed within the internal radial groove 27. In this regard, the flanges 30 and 32 can be disposed within the internal radial groove 27 by directing the flanges 30 and 32 toward the notched portions 20 and 22 of the cylindrical portion 18 until the flanges 30 and 32 engage the internal radial groove 27. When the flanges 30 and 32 are placed within the internal radial groove 27 in this manner, the cylindrical portion 18 and hence the abrading surface 12 is able to rotate with respect to the positioning member 28. However, because the positioning member 28 cannot be removed from the cylindrical portion 18 except when the flanges 30 and 32 are aligned with the notched portions 20 and 22, there is a reduced tendency of the positioning member 28 to be inadvertently displaced from the cylindrical portion 18 during usage.

The positioning member 28 also includes an angulated bore 34. The angulated bore 34 of the positioning member 28 is angularly displaced from the axial centerline of the positioning member 28 by the valgus angle of the femur. In addition, the cross-section of the angulated bore 34 is non-circular so as to engage a portion of the intramedullary rod described below which is also non-circular. While only one positioning member 28 is shown, it will be appreciated that the set of surgical instruments of the present invention includes a plurality of positioning members 28 having angulated bores 34 which generally correspond to the various possible ranges of valgus angles. In this regard, the angular displacement of the angulated bores 34 from the axial centerline of the positioning member 28 may typically be 0°, 3°, 5°, 7° and 9° according to the preferred embodiment of the present invention. However, other suitable angles may be used.

To provide means for aligning instrumentation used to shape the distal surface of the femur, an intramedullary rod 36 is provided. The intramedullary rod 36 is operable to be inserted into the intramedullary canal of the femur. Once inserted into the intramedullary canal, the femoral planer 10 as well as the cutting and resection guides described below can be mounted on the intramedullary rod 36 and therefore be positioned with respect to the intramedullary canal of the femur. The intramedullary rod 36 is substantially straight and comprises a plurality of fins 38 which are used to reduce the tendency of the intramedullary rod 36 to rotate within the intramedullary canal. In addition, the intramedullary rod 36 includes two flat portions 37 in the region where the positioning member 38 engages the intramedullary rod 36. The flat portions 37 cooperate with the non-circular cross-section of the angulated bore 34 so as to prevent rotation of the positioning member 28.

Figure 6:
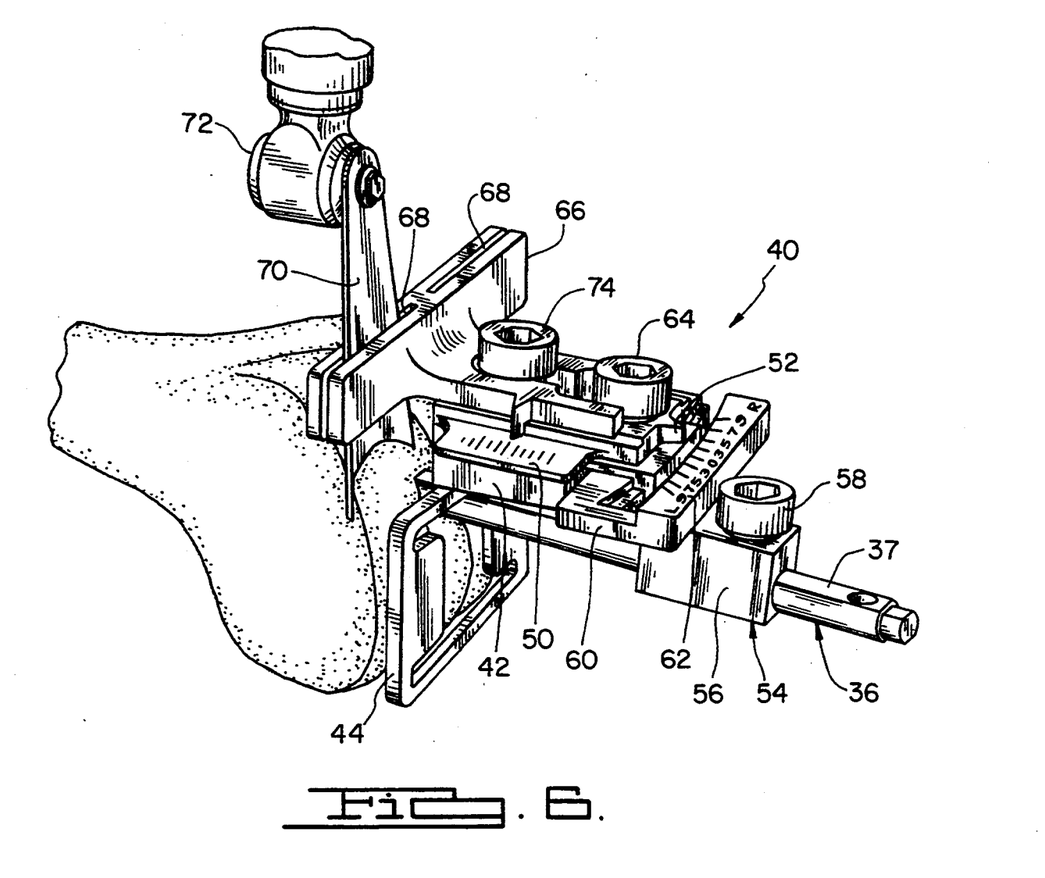
FIG. 6 is a perspective view of a distal resection guide according to the teachings of the preferred embodiment of the present invention.

To provide means for resecting the distal femur, a distal resection guide 40 is provided as shown in FIG. 6. The distal resection guide 40 includes a body member 42 which is able to be secured at a desired angular position with respect to the intramedullary rod 36. The body member 42 includes a stop plate 44 which is operable to be disposed adjacent the natural condyles 46 of the femur 48. In addition, the body member 42 includes a plurality of scale markings 50 which are able to determine the relative position of a guide member described below with respect to the condyles 46 so as to allow the surgeon to locate the position where the distal resection should be made. In addition, the body member 42 includes an indicator portion 52 which is used to indicate the angular displacement of the body member 42 with respect to the intramedullary rod 36 in a manner described below.

To support the distal resection guide 40 on the intramedullary rod 36, the distal resection guide further includes a support member 54. The support member 54 is operable to slidably engage the intramedullary rod 36 so as to secure the distal resection guide 40 to the intramedullary rod 36. The support member 54 includes a rectangularly-shaped base member 56 having a first bore which is able to receive the intramedullary rod 36. The support member 54 further includes an attachment screw 58 which is able to threadably engage a second bore in the base member 56. When the attachment screw 58 is rotated in a first direction, the attachment screw 58 is able to engage the intramedullary rod 36 so as to secure the intramedullary rod 36 to the support member 54. When the attachment screw 58 is rotated in a second direction, the attachment screw 58 is able to disengage from the intramedullary rod 36 so as to allow the support member 54 to be slidably displaced on the intramedullary rod 36.

To allow a visual indication of the orientation of the stop plate 44 with respect to the intramedullary rod 36, the distal resection guide 40 further includes a valgus angle indication member 60. The valgus angle indication member 60 is secured to the support member 54 and has a plurality of scaled markings 62 disposed thereon. The scaled markings 62 are used together with the indicator portion 52 of the body member 42 to provide an indication of the angular orientation of the body member 42 with respect to the intramedullary rod 36 so as to allow this orientation to correspond to the valgus angle of the femur 48. To adjust the angular position of the body member 42 with respect to the intramedullary rod 36, an angular adjustment screw 64 is provided. When the angular adjustment screw 64 is rotated in one direction, the angular adjustment screw 64 causes frictional engagement between the body member 42 and the support member 54 so as to provide a relatively secure engagement therebetween. When the angular adjustment screw 64 is rotated in a second direction, the body member 42 is able to be angularly displaced by sliding the indication member 60 with respect to the support member 54 so as to allow the angular position of the body member 42 with respect to the intramedullary rod 36 to be adjusted corresponding to the valgus angle of the femur 48.

The distal resection guide 40 further includes a guide member 66. The guide member 66 includes two slots 68 which are operable to receive and guide the cutting blade 70 of a saw 72 during resection. The guide member 66 is disposed on the upper surface of the body member 42 and includes a plurality of grooves on its lower surface which are operable to engage a plurality of grooves located on the upper surface of the body member 42. To secure the guide member 66 to the body member 42, a guide adjustment screw 74 is provided. The guide adjustment screw 74 is operable to engage both the guide member 66 and the body member 42 so as to cause selective engagement therebetween. In this regard, when the guide adjustment screw 74 is rotated in a first direction, the guide adjustment screw 74 causes relatively secure engagement between the guide member 66 and the body member 42. When the guide adjustment screw 74 is rotated in a second direction, the guide member 66 is able to be longitudinally displaced with respect to the body member 42 so as to adjust the position of the guide member 66 with respect to the condyles 46 of the femur 48.

Figure 8:
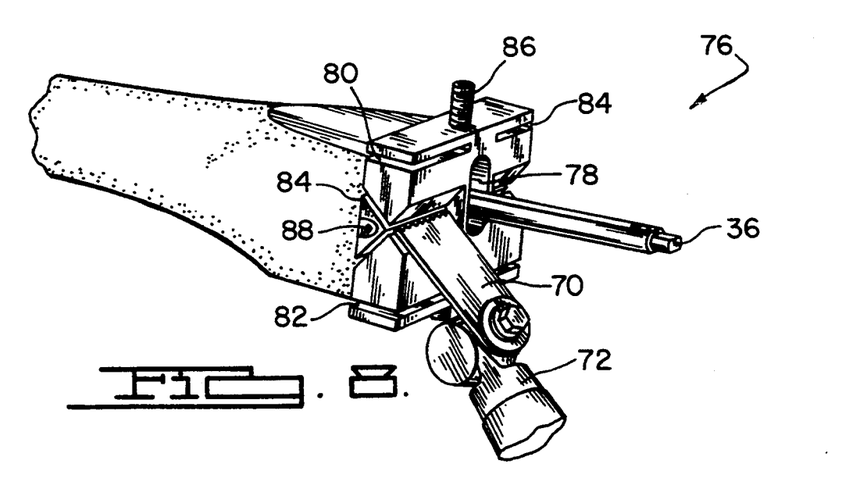
FIG. 8 is a perspective view of the distal cutting guide according to the teachings of the preferred embodiment of the present invention.

To provide means for guiding the anterior, posterior and chamfer resection of the femur, a cutting block 76 is provided as shown in FIG. 8. The cutting block 76 is operable to be secured to the femur 48 and to orient the cutting blade 70 so as to guide the anterior, posterior and chamfer resection of the femur 48. The cutting block 76 includes a centrally disposed bore 78 which is operable to receive the intramedullary rod 36. In addition, the cutting block 76 includes a plurality of guide slots 80–84 which are used for resecting the femur 48. The guide slots 80 and 82 are used during the anterior and posterior resection of the femur 48 respectively, while the guide slots 84 are used to guide the chamfer resection of the femur 48. The cutting block 76 is secured in a position adjacent to the femur 48 by means of two attachment bolts 86. The attachment bolts 86 are operable to threadably engage apertures in the upper and lower surface of the cutting block 76 and is able to selectively engage the intramedullary rod 36 when the intramedullary rod 36 is located within the bore 78 of the cutting block 76. Accordingly, when the attachment bolts 86 are rotated in the direction so as to cause the attachment bolts 86 to engage the intramedullary rod 36, the cutting block 76 may be secured to the intramedullary rod 36. As will be appreciated by those skilled in the art, the degree to which each of the attachment bolts 86 are rotated when they engage the intramedullary rod 36 determines the anterior-posterior position of the intramedullary rod 36 within the bone 78. The cutting block 76 also includes a nail 88 which is operable to be inserted from the cutting block 76 to the femur 48 so as to further secure the cutting block 76 to the femur 48.

A description of the method of using the surgical instruments discussed above will now be presented. It will be noted that only a single intramedullary rod 36 is used to prepare the femur 48 regardless of the valgus angle of the femur 48. In addition, the intramedullary rod 36 is substantially straight so that it is relatively easy to impact the intramedullary rod 36 into the femur 48. Finally, it should be appreciated that the following method is only one embodiment of the present invention and that other methods will become apparent to those skilled in the art.

Figure 4:
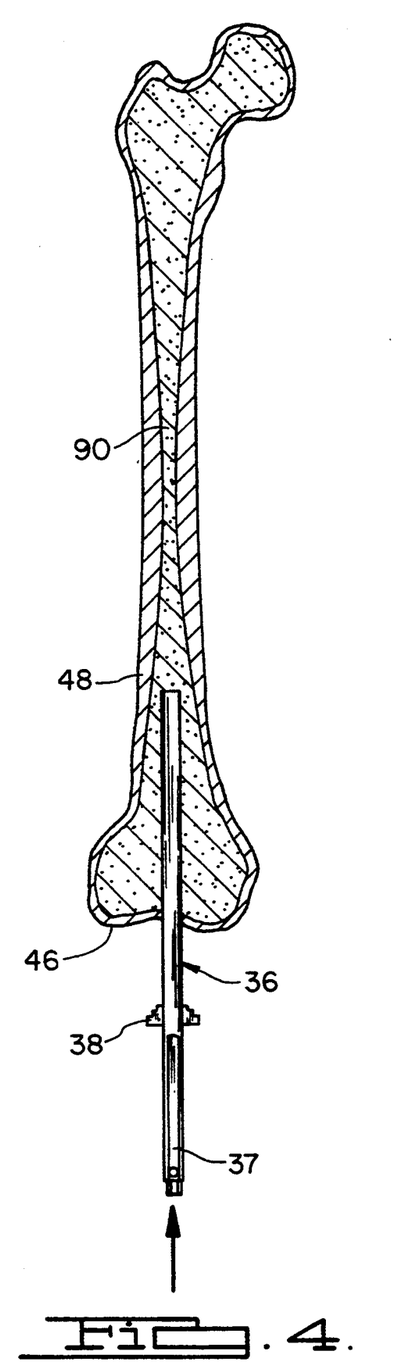
FIG. 4 is a cross-sectional view of a femur showing an intramedullary rod partially inserted into the intramedullary canal of the femur according to the teachings of the preferred embodiment of the present invention.
Figure 5:
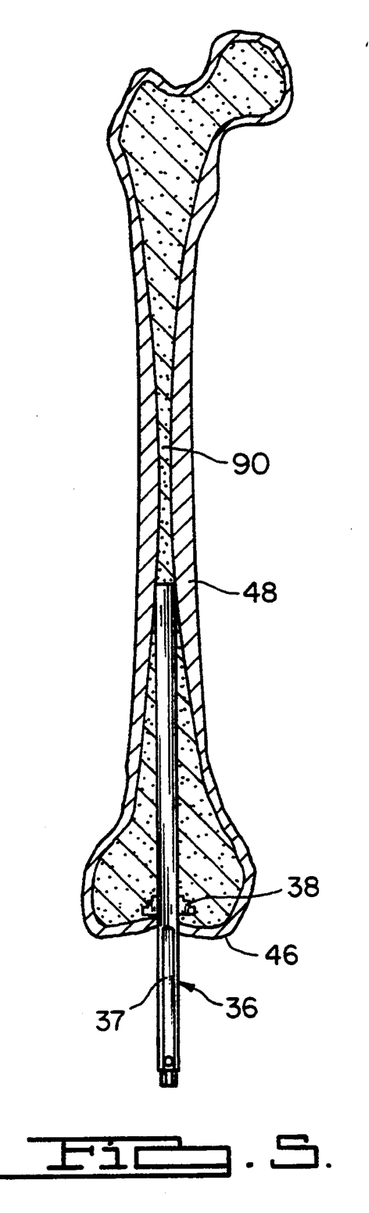
FIG. 5 is a cross-sectional view of a femur showing the intramedullary rod of FIG. 4 being fully inserted into the intramedullary canal of the femur according to the teachings of the preferred embodiment of the present invention.

The valgus angle of the femur 48 is determined preoperatively using methods well-known in the art, such as by radiographic examination. A hole is first drilled in the distal surface of the intracondylar notch of the femur 48 to form an entry point for the intramedullary rod 36. As shown in FIGS. 4 and 5, after the hole is drilled in the intramedullary canal 90, the intramedullary rod 36 is impacted into the intramedullary canal 90 until the fins 38 of the intramedullary rod 36 engage the femur 48. When engaged in this manner, the fins 38 reduce the tendency of the intramedullary rod 36 to rotate within the intramedullary canal 90. As will be appreciated by those skilled in the art, however, the distal resection guide 40 may be initially mounted on the intramedullary rod 36 before the intramedullary rod 36 is inserted into the intramedullary canal 90. In doing so, care is taken to rotationally position the intramedullary rod 36 and therefore the distal resection guide 40 such that approximately an equal amount of bone is disposed on each side of the lowermost portion of the stop plate 44. The intramedullary rod 36 preferably extends approximately 8.5 inches in the femur 48 and therefor does not enter the narrowest portion of the intramedullary canal 90.

After the intramedullary rod 36 has been inserted into the femur 48, the distal resection of the femur 48 is performed as shown in FIG. 6. In this regard, the body member 42 is first angularly adjusted with respect to the support member 54 until the indicator portion 52 of the body member 42 indicates the valgus angle of the femur 48 on the valgus angle indication member 60. The angular adjustment screw 64 is then rotated until the body member 42 is positionally secured to the support member 54. The guide member 66 is then longitudinally displaced with respect to the body member 42 by the amount of bone to be removed from the distal end of the femur 48, then the guide adjustment screw 74 is rotated to positionably secure the guide member 66 to the body member 42. The distal resection guide 40 is placed adjacent to the distal portion of the femur 48 by inserting the intramedullary rod 36 into the first bore of the base member 56. The attachment screw 58 is then rotated until the base member 56 is positionally secured to the intramedullary rod 36.

After the distal resection guide 40 is secured to the intramedullary rod 36, the cutting blade 70 is inserted into the slots 68 of the distal resection guide 40 and then distal resection is performed. The distal resection guide 40 is then removed from the intramedullary rod 36.

Figure 7:
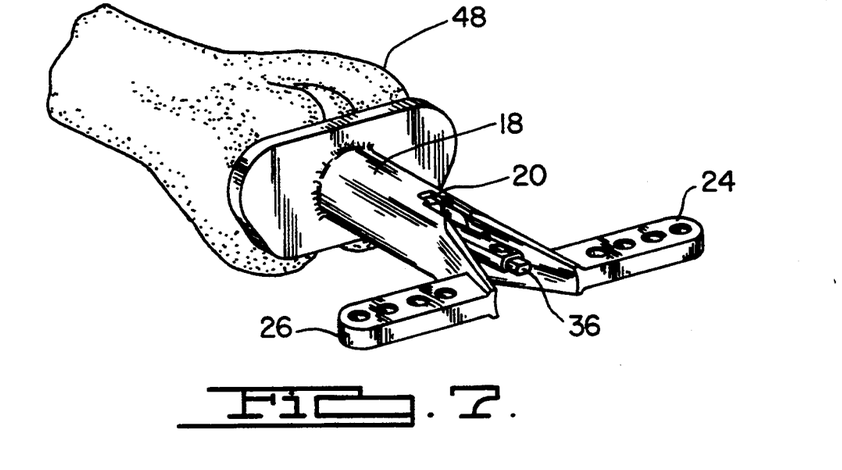
FIG. 7 is a perspective view of the femoral planer shown as engaging an intramedullary rod according to the teachings of the preferred embodiment of the present invention.

A positioning member 28 is then chosen which has an angulated bore 34 which corresponds to the valgus angle of the femur 48 as previously determined. The positioning member 28 is then inserted into the cylindrical portion 18 of the femoral planer 10 of the femoral planer 10 by aligning the flanges 30 and 32 of the positioning member 28 with the notched portions 20 and 22 of the cylindrical portion 18. Care is taken to insure that the positioning member 28 is properly inserted into the cylindrical portion 18 so as to reflect the fact that the femur 48 is left or right. The intramedullary rod 36 is then inserted through the aperture 16 in the femoral planer 10 and angulated bore 34 in the positioning member 28 until the abrading surface 12 of the femoral planer 10 contacts the distal surface of the femur 48. The abrading surface 12 is rotated about the distal surface of the femur 48 by imparting a twisting motion to the handles 24 and 26 of the femoral planer 10. When the distal surface of the femur 48 has been abraded to produce a relatively smooth surface, the femoral planer 10 is removed from the intramedullary rod 36.

Figure 9:
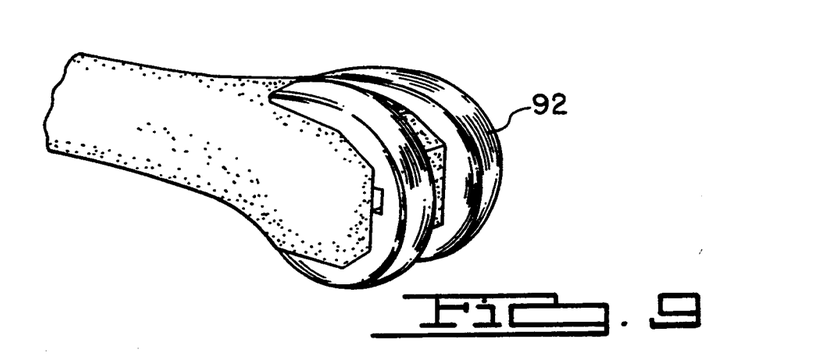
FIG. 9 is a perspective view of a femur with a prosthetic device being secured thereto, the femur being shaped according to the teachings of the preferred embodiment of the present invention.

After the femoral planer 10 has been used to smooth the distal surface of the femur 48, the cutting block 76 is used to perform the anterior, posterior and chamfer resection of the femur 48 as shown in FIG. 8. In this regard, the cutting block 76 is first positioned on the intramedullary rod 36 such that the cutting block 76 contacts the femur 48. The attachment bolts 86 are then rotated so as to engage the intramedullary rod 36 at the desired position within the bone 78, while the nail 88 is inserted through the cutting block 76 into the femur 48 so as to secure the cutting block 76 to the femur 48. Anterior resection of the femur 48 is performed using guide slots 80 and the cutting blade 70, while posterior resection of the femur 48 is performed using guide slots 82. Finally, the chamfer resection of the femur 48 is performed using guide slots 84 of the cutting block 76. The cutting block 76 is then removed from the intramedullary rod 36. A prosthetic device 92 in the form of a femoral component of a knee joint prosthesis may then be secured to the distal end of the femur 48 as shown in FIG. 9 in a manner well-known in the art.

Those skilled in the art can now appreciate from the foregoing description that the broad teachings of the present invention can be implemented in a variety of forms. For example, the intramedullary canal may be reamed before the intramedullary rod is inserted into the femur. In addition, while the present invention has been described as being used in conjunction with the femur, it will be appreciated that the present invention may also be used with other bones as well. Furthermore, the positioning members can be used with both left and right femurs by simply rotating the positioning member by 180° along the central axis of the positioning member. Therefore, while this invention has been described in connection with particular examples thereof, the true scope of the invention should not be so limited since other modifications will become apparent to those skilled in the art.

What is claimed is:

1. A set of surgical instruments for shaping an end of a bone to prepare the bone for receiving a prosthetic device, said set of surgical instruments comprising:
    an intramedullary rod being operable to be secured to the bone, said intramedullary rod being substantially straight and having a portion of which is operable to protrude from the bone;
    a planer operable to shape the end of the bone, said planer including:
    (a) a planing surface being operable to abrade the end of the bone; and
    (b) orienting means for orienting said planing surface of said planer at any predetermined one of a plurality of different angular orientations with respect to said protruding portion of said substantially straight intramedullary rod, said orienting means having a first surface which is operable to non-rotationally engage said intramedullary rod, said orienting means further having a second surface being operable to permit said planing surface to rotate with respect to said intramedullary rod;
    whereby said planer is operable to shape the end of the bone at said predetermined one of said plurality of different angular orientations.

2. The set of surgical instruments according to claim 1, wherein said orienting means for orienting said surface of said planar at any predetermined one of said plurality of different angular orientations comprises a plurality of interchangeable angular positioning members, each of which correspond to one of said different angular orientations.

3. The set of surgical instruments according to claim 2, wherein at least one of said angular positioning members has a bore extending therethrough at an angulated orientation with respect thereto for nonrotatably receiving said protruding portion of said substantially straight intramedullary rod therein, the angle associated with said bore being operable to determine the angle at which said planing surface shapes the end of the bone with respect to said protruding portion of said intramedullary rod.

4. The set of surgical instruments according to claim 1, wherein said orienting means comprises at least one angular positioning member being operable to be removably secured to said planer, said one angular positioning member having a bore extending therethrough at an angulated non-coaxial orientation with respect thereto for nonrotatably receiving said protruding portion of said intramedullary rod therein and being operable to determine said predetermined one of said plurality of different angular orientations at which said planing surface shapes the end of the bone.

5. The set of surgical instruments according to claim 1, wherein said orienting means comprises:
(a) a plurality of angular positioning members, each of said angular positioning members having a cylindrical outer surface and including: a bore extending therethrough at an angulated non-coaxial orientation with respect thereto for nonrotatably receiving said protruding portion of said substantially straight intramedullary rod therein and corresponding to said predetermined one of said plurality of different angular orientations and, means for permitting limited movement of said angular positioning member with respect to said planing surface; and
(b) a portion of said planer secured to said planing surface and having a cylindrical bore therein operable to removably receive each of said plurality of angular positioning members so that said planer can be rotated with respect to each of said angular positioning members upon being received by said cylindrical bore.

6. A set of surgical instruments for shaping an end of a bone to prepare the bone for resection prior to receiving a prosthetic device, said set of surgical instruments comprising:
a rod member being operable to be secured to the bone, said rod member being substantially straight and having a portion which is operable to protrude from the bone;
a planer being operable to engage the periphery of said protruding portion of said substantially straight rod member, said planer being further operable to selectively abrade the end of the bone at one of a plurality of pre-selected angular orientations with respect to said protruding portion of said substantially straight rod member, said planer including:
(a) a planing surface being operable to abrade the end of the bone, and
(b) orienting means for orienting said planing surface of said planer at any predetermined one of a plurality of different angular orientations with respect to said protruding portion of said substantially straight rod member, said orienting means having a first surface which is operable to non-rotationally engage said substantially straight rod member, said orienting means further having a second surface being operable to permit said planing surface to rotate with respect to said substantially straight rod member; and
whereby said planer is operable to abrade the end of the bone so as to fore a surface for establishing in part the position of the resection of said bone.

7. The set of surgical instruments according to claim 6, wherein said rod member is operable to be secured to the bone so as to establish at least in part the angular orientation of said planer with respect to the bone.

8. The set of surgical instruments according to claim 7, wherein the bone has an intramedullary canal extending longitudinally therethrough, said rod member is operable to be disposed within the intramedullary canal of the bone.

9. The set of surgical instruments according to claim 6, wherein said orienting means includes a plurality of angular positioning members, each of said angular positioning members corresponding to one of said different pre-selected angular orientations.

10. The set of surgical instruments according to claim 9, wherein at least one of said angular positioning members has a bore extending therethrough at an angulated orientation with respect thereto for nonrotatably receiving said protruding portion of said substantially straight rod member therein, the angle associated with said angularly-extending bore being operable to determine said predetermined one of said plurality of different pre-selected angular orientations at which said planing surface shapes the end of the bone.

11. The set of surgical instruments according to claim 6, wherein said orienting means includes at least one angular positioning member being operable to be removably secured to said planer, said one positioning member having a bore extending at an angular orientation therein and being operable to determine the angle at which said planing surface shapes the end of the bone.

12. The set of surgical instruments according to claim 6, wherein said orienting means comprises:
(a) a plurality of generally cylindrical angular positioning members, each of said positioning members including:
a non-coaxial bore extending therethrough at an angulated orientation relative thereto for nonrotatably receiving a portion of said straight rod member therein and corresponding to said predetermined one of said plurality of different angular orientations;
means for permitting limited movement of said angular positioning member with respect to said planing surface; and
(b) a portion of said planer secured to said planing surface and having a cylindrical bore therein operable to removably receive each of said plurality of generally cylindrical angular positioning members.

13. The set of surgical instruments according to claim 6, further comprising a distal resection guide having:
(a) a first member being operable to be removably secured to said substantially straight rod member;
(b) a second member being operable to engage the bone and being selectively angularly displaceable with respect to said first member; and
(c) a third member being operable to guide the resection of a portion of the bone, said third member being longitudinally displaceable with respect to said second member;
said distal resection guide being operable to accurately guide the resection of an area adjacent the end of the bone with respect to both the end of the bone and said rod member.

14. A method for shaping an end of a bone for preparing the bone for receiving a prosthetic device, the bone having a predeterminable valgus angle associated therewith, said method comprising the steps of:
securing an intramedullary rod to the bone, said intramedullary rod being substantially straight and having a protruding portion operable to extend from the bone;
preparing a planer to abrade the end of the bone, said planer including:
(a) a planing surface being operable to abrade the and of the bone, and
(b) orienting means for orienting said planing surface of said planer at any predetermined one of a plurality of different angular orientations with respect to said protruding portion of said substantially straight intramedullary rod, said orienting means having a first surface which is operable to non-rotationally engage said intramedullary rod, said orienting means further having a second surface being operable to permit said planing surface to rotate with respect to said intramedullary rod;

locating said planer adjacent to the end of the bone at a predetermined one of said plurality of different angular orientations with respect to said substantially straight intramedullary rod; and rotating said planer so as to abrade the end of the bone.

15. The method according to claim 14, further comprising the additional step of removably securing one of a plurality of angular positioning members to said planer, each of said angular positioning members having a bore extending therethrough at an angular orientation relative thereto for removably receiving a portion of said straight intramedullary rod therein.

16. The method according to claim 15, wherein said method further includes the additional step of selecting one of said positioning members that has an angular bore that most closely corresponds to the valgus angle of the bone.

17. The method of claim 16, wherein said step of locating a planer adjacent to end of the bone includes the step of disposing a portion of said straight intramedullary rod in said angular bore of said one angular positioning member.

18. The method according to claim 17, wherein said planer includes a portion having a cylindrical bore therein, and said one angular positioning member has a cylindrical outer surface thereon with said angular bore therethrough being non-coaxial with respect thereto, said method further comprising the additional step of inserting said one angular positioning member into said cylindrical bore in said portion of said planer to thereby establish one of said predetermined angular orientations.

19. The method of claim 14, wherein said step of securing said intramedullary rod to the bone includes the step of impacting said substantially straight intramedullary rod along the axial centerline of said substantially straight intramedullary rod.

* * * * *